United States Patent
Armstrong et al.

(10) Patent No.: US 8,942,798 B2
(45) Date of Patent: Jan. 27, 2015

(54) ALTERNATIVE OPERATION MODE FOR AN IMPLANTABLE MEDICAL DEVICE BASED UPON LEAD CONDITION

(75) Inventors: Randolph K. Armstrong, Houston, TX (US); Albert A. Rodriguez, Friendswood, TX (US); Steven E. Maschino, Seabrook, TX (US)

(73) Assignee: Cyberonics, Inc., Houston, TX (US)

( * ) Notice: Subject to any disclaimer, the term of this patent is extended or adjusted under 35 U.S.C. 154(b) by 1927 days.

(21) Appl. No.: 11/925,746

(22) Filed: Oct. 26, 2007

(65) Prior Publication Data
US 2009/0125079 A1    May 14, 2009

(51) Int. Cl.
*A61N 1/32* (2006.01)
*A61N 1/05* (2006.01)
*A61N 1/36* (2006.01)
*A61N 1/08* (2006.01)

(52) U.S. Cl.
CPC ............ *A61N 1/0551* (2013.01); *A61N 1/3605* (2013.01); *A61N 1/0558* (2013.01); *A61N 1/36082* (2013.01); *A61N 2001/083* (2013.01)
USPC ............ 607/2; 607/8; 607/9; 607/27; 607/45; 607/118

(58) Field of Classification Search
CPC .............. A61N 1/0551; A61N 1/3605; A61N 2001/083
USPC ........................................ 607/2, 8–9, 27, 118
See application file for complete search history.

(56) References Cited

U.S. PATENT DOCUMENTS

| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |

(Continued)

FOREIGN PATENT DOCUMENTS

WO    2004/069330    8/2004

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

(Continued)

*Primary Examiner* — Carl H Layno
*Assistant Examiner* — Jennifer Ghand
(74) *Attorney, Agent, or Firm* — Cyberonics, Inc.

(57) ABSTRACT

A method, apparatus, and system for determining an adverse operational condition associated with a lead assembly in an implantable medical device used for providing a therapeutic electrical signal to a cranial nerve. A first impedance associated with the lead assembly configured to provide the therapeutic electrical signal to a cranial nerve is detected. A determination is made as to whether the first impedance is outside a first predetermined range. A second impedance is detected. The detection of the second impedance is performed within a predetermined period of time from the time of the detection of the first impedance. A determination is made as to whether the second impedance is outside a second predetermined range. If the first impedance is outside the first range and the second impedance is outside the second range, the implantable medical device is prevented from providing the therapeutic electrical signal.

24 Claims, 10 Drawing Sheets

(56) References Cited

U.S. PATENT DOCUMENTS

| | | | | |
|---|---|---|---|---|
| 4,305,402 A | | 12/1981 | Katims | |
| 4,384,926 A | | 5/1983 | Wagner | |
| 4,407,303 A | | 10/1983 | Akerstrom | |
| 4,458,696 A | | 7/1984 | Larimore | |
| 4,459,989 A | | 7/1984 | Borkan | |
| 4,573,481 A | | 3/1986 | Bullara | |
| 4,590,946 A | | 5/1986 | Loeb | |
| 4,592,359 A | | 6/1986 | Galbraith | |
| 4,606,349 A | | 8/1986 | Livingston et al. | |
| 4,608,985 A | | 9/1986 | Crish et al. | |
| 4,612,934 A | | 9/1986 | Borkan | |
| 4,628,942 A | | 12/1986 | Sweeney et al. | |
| 4,630,615 A | | 12/1986 | Yomtov | |
| 4,649,936 A | | 3/1987 | Ungar et al. | |
| 4,702,254 A | | 10/1987 | Zabara | |
| 4,793,353 A | | 12/1988 | Borkan | |
| 4,821,724 A | | 4/1989 | Whigham et al. | |
| 4,827,932 A | | 5/1989 | Ideker et al. | |
| 4,850,356 A | | 7/1989 | Heath | |
| 4,860,616 A | | 8/1989 | Smith | |
| 4,867,164 A | | 9/1989 | Zabara | |
| 4,870,341 A | * | 9/1989 | Pihl et al. | 324/600 |
| 4,899,750 A | | 2/1990 | Ekwall | |
| 4,903,700 A | | 2/1990 | Whigham et al. | |
| 4,920,979 A | | 5/1990 | Bullara | |
| 4,964,407 A | | 10/1990 | Baker, Jr. et al. | |
| 4,969,468 A | | 11/1990 | Byers et al. | |
| 4,979,511 A | | 12/1990 | Terry, Jr. | |
| 5,003,975 A | * | 4/1991 | Hafelfinger et al. | 607/28 |
| 5,025,807 A | | 6/1991 | Zabara | |
| 5,095,905 A | | 3/1992 | Klepinski | |
| 5,111,815 A | | 5/1992 | Mower | |
| 5,137,020 A | | 8/1992 | Wayne et al. | |
| 5,137,021 A | | 8/1992 | Wayne et al. | |
| 5,139,028 A | | 8/1992 | Steinhaus et al. | |
| 5,146,920 A | | 9/1992 | Yuuchi et al. | |
| 5,154,172 A | | 10/1992 | Terry, Jr. et al. | |
| 5,179,950 A | | 1/1993 | Stanislaw | |
| 5,186,170 A | | 2/1993 | Varrichio et al. | |
| 5,188,104 A | | 2/1993 | Wernicke et al. | |
| 5,201,808 A | | 4/1993 | Steinhaus et al. | |
| 5,201,865 A | | 4/1993 | Kuehn | |
| 5,205,285 A | | 4/1993 | Baker, Jr. | |
| 5,215,086 A | | 6/1993 | Terry, Jr. et al. | |
| 5,215,089 A | | 6/1993 | Baker, Jr. | |
| 5,222,494 A | | 6/1993 | Baker, Jr. | |
| 5,231,988 A | | 8/1993 | Wernicke et al. | |
| 5,237,991 A | | 8/1993 | Baker, Jr. et al. | |
| 5,251,634 A | | 10/1993 | Weinberg | |
| 5,263,480 A | | 11/1993 | Wernicke et al. | |
| 5,269,303 A | | 12/1993 | Wernicke et al. | |
| 5,299,569 A | | 4/1994 | Wernicke et al. | |
| 5,304,206 A | | 4/1994 | Baker, Jr. et al. | |
| 5,330,515 A | | 7/1994 | Rutecki et al. | |
| 5,335,657 A | | 8/1994 | Terry, Jr. et al. | |
| 5,351,394 A | | 10/1994 | Weinberg | |
| 5,411,528 A | | 5/1995 | Miller et al. | |
| 5,431,692 A | | 7/1995 | Hansen et al. | |
| 5,466,255 A | | 11/1995 | Franchi | |
| 5,501,702 A | | 3/1996 | Plicchi et al. | |
| 5,507,786 A | * | 4/1996 | Morgan et al. | 607/27 |
| 5,522,865 A | | 6/1996 | Schulman et al. | |
| 5,531,778 A | | 7/1996 | Maschino et al. | |
| 5,534,018 A | | 7/1996 | Wahlstrand et al. | |
| 5,540,730 A | | 7/1996 | Terry, Jr. et al. | |
| 5,540,734 A | | 7/1996 | Zabara | |
| 5,549,646 A | * | 8/1996 | Katz et al. | 607/8 |
| 5,571,150 A | | 11/1996 | Wernicke et al. | |
| 5,575,813 A | | 11/1996 | Edell et al. | |
| 5,620,474 A | | 4/1997 | Koopman | |
| 5,658,318 A | | 8/1997 | Stroetmann et al. | |
| 5,690,681 A | | 11/1997 | Geddes et al. | |
| 5,700,282 A | | 12/1997 | Zabara | |
| 5,707,400 A | | 1/1998 | Terry, Jr. et al. | |
| 5,713,936 A | | 2/1998 | Staub et al. | |
| 5,741,311 A | | 4/1998 | Mc Venes et al. | |
| 5,743,860 A | | 4/1998 | Hively et al. | |
| 5,755,742 A | * | 5/1998 | Schuelke et al. | 607/27 |
| 5,755,747 A | | 5/1998 | Daly et al. | |
| 5,759,199 A | | 6/1998 | Snell et al. | |
| 5,769,873 A | | 6/1998 | Zadeh | |
| 5,796,044 A | | 8/1998 | Cobian et al. | |
| 5,814,088 A | * | 9/1998 | Paul et al. | 607/28 |
| 5,876,425 A | | 3/1999 | Gord et al. | |
| 5,891,179 A | * | 4/1999 | Er et al. | 607/27 |
| 5,897,577 A | | 4/1999 | Cinbis et al. | |
| 5,916,239 A | | 6/1999 | Geddes et al. | |
| 5,919,220 A | | 7/1999 | Stieglitz et al. | |
| 5,928,272 A | | 7/1999 | Adkins et al. | |
| 5,995,868 A | | 11/1999 | Osorio et al. | |
| 6,035,237 A | | 3/2000 | Schulman et al. | |
| 6,052,624 A | | 4/2000 | Mann | |
| 6,073,050 A | | 6/2000 | Griffith | |
| 6,104,956 A | | 8/2000 | Naritoku et al. | |
| 6,154,678 A | | 11/2000 | Lauro | |
| 6,171,239 B1 | | 1/2001 | Humphrey | |
| 6,181,969 B1 | | 1/2001 | Gord | |
| 6,208,902 B1 | | 3/2001 | Boveja | |
| 6,212,431 B1 | | 4/2001 | Hahn et al. | |
| 6,216,045 B1 | | 4/2001 | Black et al. | |
| 6,259,951 B1 | | 7/2001 | Kuzma et al. | |
| 6,269,270 B1 | | 7/2001 | Boveja | |
| 6,304,787 B1 | | 10/2001 | Kuzma et al. | |
| 6,317,633 B1 | | 11/2001 | Jorgenson et al. | |
| 6,339,725 B1 | | 1/2002 | Naritoku et al. | |
| 6,341,236 B1 | | 1/2002 | Osorio et al. | |
| 6,393,325 B1 | | 5/2002 | Mann et al. | |
| 6,400,988 B1 | | 6/2002 | Gurewitsch | |
| 6,418,348 B1 | | 7/2002 | Witte | |
| 6,445,951 B1 | | 9/2002 | Mouchawar | |
| 6,453,198 B1 | | 9/2002 | Torgerson et al. | |
| 6,456,481 B1 | | 9/2002 | Stevenson | |
| 6,473,653 B1 | | 10/2002 | Schallhorn et al. | |
| 6,477,417 B1 | | 11/2002 | Levine | |
| 6,490,486 B1 | | 12/2002 | Bradley | |
| 6,505,074 B2 | | 1/2003 | Boveja et al. | |
| 6,510,332 B1 | | 1/2003 | Greenstein | |
| 6,529,774 B1 | | 3/2003 | Greene | |
| 6,553,263 B1 | | 4/2003 | Meadows et al. | |
| 6,556,868 B2 | | 4/2003 | Naritoku et al. | |
| 6,587,719 B1 | | 7/2003 | Barrett et al. | |
| 6,587,727 B2 | | 7/2003 | Osorio et al. | |
| 6,600,956 B2 | | 7/2003 | Maschino et al. | |
| 6,600,957 B2 | | 7/2003 | Gadsby | |
| 6,606,523 B1 | | 8/2003 | Jenkins | |
| 6,609,025 B2 | | 8/2003 | Barrett et al. | |
| 6,620,186 B2 | | 9/2003 | Saphon et al. | |
| 6,622,038 B2 | | 9/2003 | Barrett et al. | |
| 6,622,041 B2 | | 9/2003 | Terry, Jr. et al. | |
| 6,622,047 B2 | | 9/2003 | Barrett et al. | |
| 6,648,823 B2 | | 11/2003 | Thompson | |
| 6,658,294 B1 | | 12/2003 | Zadeh et al. | |
| 6,662,053 B2 | | 12/2003 | Borkan | |
| 6,671,556 B2 | | 12/2003 | Osorio et al. | |
| 6,684,105 B2 | | 1/2004 | Cohen et al. | |
| 6,687,538 B1 | | 2/2004 | Hrdlicka et al. | |
| 6,690,974 B2 | | 2/2004 | Archer et al. | |
| 6,711,440 B2 | | 3/2004 | Deal et al. | |
| 6,718,203 B2 | | 4/2004 | Weiner et al. | |
| 6,718,207 B2 | | 4/2004 | Connelly | |
| 6,721,600 B2 | | 4/2004 | Jorgenson et al. | |
| 6,721,603 B2 | | 4/2004 | Zabara et al. | |
| 6,725,092 B2 | | 4/2004 | MacDonald et al. | |
| 6,731,979 B2 | | 5/2004 | MacDonald | |
| 6,745,077 B1 | | 6/2004 | Griffith et al. | |
| 6,754,539 B1 | | 6/2004 | Erickson et al. | |
| 6,757,566 B2 | | 6/2004 | Weiner et al. | |
| 6,760,624 B2 | | 7/2004 | Anderson et al. | |
| 6,760,625 B1 | | 7/2004 | Kroll | |
| 6,760,628 B2 | | 7/2004 | Weiner et al. | |
| 6,763,268 B2 | | 7/2004 | MacDonald et al. | |
| 6,778,856 B2 | | 8/2004 | Connelly et al. | |
| 6,792,316 B2 | | 9/2004 | Sass | |
| 6,795,730 B2 | | 9/2004 | Connelly et al. | |

(56) References Cited

U.S. PATENT DOCUMENTS

| | | |
|---|---|---|
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 | 1/2005 | Bluger |
| 6,845,266 B2 | 1/2005 | Weiner et al. |
| 6,850,805 B2 | 2/2005 | Connelly et al. |
| 6,875,180 B2 | 4/2005 | Weiner et al. |
| 6,901,290 B2 | 5/2005 | Foster et al. |
| 6,906,256 B1 | 6/2005 | Wang |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |
| 7,006,859 B1 | 2/2006 | Osorio et al. |
| 7,010,357 B2 | 3/2006 | Helfer et al. |
| 7,013,174 B2 | 3/2006 | Connelly et al. |
| 7,015,393 B2 | 3/2006 | Weiner et al. |
| 7,047,074 B2 | 5/2006 | Connelly et al. |
| 7,050,851 B2 * | 5/2006 | Plombon et al. ............ 607/8 |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 | 2/2007 | Wahlstrand et al. |
| 7,212,869 B2 | 5/2007 | Wahlstrom |
| 7,221,981 B2 | 5/2007 | Gliner |
| 7,239,924 B2 | 7/2007 | Kolberg |
| 7,289,856 B1 | 10/2007 | Karicherla |
| 7,584,004 B2 | 9/2009 | Caparso et al. |
| 2002/0072782 A1 | 6/2002 | Osorio et al. |
| 2002/0120307 A1 * | 8/2002 | Jorgenson et al. ............ 607/27 |
| 2003/0083726 A1 | 5/2003 | Zeijlemaker et al. |
| 2003/0195601 A1 | 10/2003 | Hung et al. |
| 2004/0015205 A1 | 1/2004 | Whitehurst et al. |
| 2004/0064161 A1 * | 4/2004 | Gunderson et al. ............ 607/28 |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 | 10/2004 | Erickson |
| 2005/0015128 A1 | 1/2005 | Rezai et al. |
| 2005/0016657 A1 | 1/2005 | Bluger |
| 2005/0096719 A1 * | 5/2005 | Hammill et al. ............ 607/122 |
| 2005/0107858 A1 | 5/2005 | Bluger |
| 2005/0137636 A1 * | 6/2005 | Gunderson et al. ............ 607/27 |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0025828 A1 * | 2/2006 | Armstrong et al. ............ 607/28 |
| 2006/0058597 A1 | 3/2006 | Machado et al. |
| 2006/0106430 A1 | 5/2006 | Fowler et al. |
| 2006/0116733 A1 * | 6/2006 | Gunderson ............ 607/27 |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker et al. |
| 2006/0247706 A1 * | 11/2006 | Germanson et al. ............ 607/27 |
| 2006/0253164 A1 | 11/2006 | Zhang et al. |
| 2006/0259078 A1 * | 11/2006 | Libbus ............ 607/2 |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1 | 5/2007 | Maschino et al. |
| 2007/0142889 A1 | 6/2007 | Whitehurst et al. |
| 2007/0173902 A1 | 7/2007 | Maschino et al. |
| 2007/0179557 A1 | 8/2007 | Maschino et al. |
| 2007/0179579 A1 | 8/2007 | Feler et al. |
| 2007/0179584 A1 | 8/2007 | Gliner |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson et al. |
| 2008/0215110 A1 | 9/2008 | Gunderson et al. |
| 2008/0255582 A1 | 10/2008 | Harris |
| 2009/0076567 A1 | 3/2009 | Fowler et al. |

OTHER PUBLICATIONS

Mesut Sahn, Improved Nerve Cuff Electrode Recordings with Sub-threshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

* cited by examiner

ALTERNATIVE OPERATION MODE FOR AN IMPLANTABLE MEDICAL DEVICE BASED UPON LEAD CONDITION

BACKGROUND OF THE INVENTION

1. Field of the Invention

This invention relates generally to implantable medical devices, and more particularly to methods, apparatus, and systems for monitoring lead health and providing an alternative operation mode for an implantable medical device based upon an assessment of the lead health/condition.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification. Electrical stimulation of the vagus nerve may be provided by implanting an electrical device underneath the skin of a patient and performing a detection and electrical stimulation process. Alternatively, the system may operate without a detection system if the patient has been diagnosed with epilepsy, and may periodically apply a series of electrical pulses to the vagus (or other cranial) nerve intermittently throughout the day, or over another predetermined time interval.

Typically, implantable medical devices (IMDs) involving the delivery of electrical pulses to body tissues, such as pacemakers (heart tissue) and vagus nerve stimulators or spinal cord stimulators (nerve tissue), comprise a pulse generator for generating the electrical pulses and a lead assembly coupled at its proximal end to the pulse generator terminals and at its distal end to one or more electrodes in contact with the body tissue to be stimulated.

Occasionally, damage to the lead assembly can occur, which may cause various operational problems. Impedance measurements may be used to assess the integrity of the electrical leads that deliver the stimulation provided by a pulse generator. A change in the impedance across the leads that deliver the electrical pulses may be indicative of either or both of changes in a patient's body or changes in the electrical leads themselves. For example, damage in the lead, which may be induced by a break in one or more filaments in a multifilament lead wire, or changes in the body tissue where stimulation is delivered, may affect the efficacy of the stimulation therapy. Therefore, it is desirable for changes in the lead impedance, which may be indicative of various changes or malfunctions, to be accurately detected.

For instance, the integrity of the leads that deliver stimulation is of interest to insure that the proper therapy dosage is delivered to the patient. Some IMDs, most notably pacemakers, provide a voltage-controlled output that is delivered to one or more body locations (typically the heart). Other IMDs, such as a vagus nerve stimulator device developed by Cyberonics, Inc., provide a current-controlled output. Generally, however, state-of-the-art measurements of lead impedance involve an analysis of the delivery of a voltage signal from a capacitive (C) energy storage component through the resistive (R) lead impedance and an examination of the decay of that signal based upon a time-constant proportional to the product of the resistance and capacitance (RC). The total equivalent impedance present at the leads and the known energy source total equivalent capacitance cause a time-constant discharge curve. As the voltage on the capacitance is discharged through the resistance, the exponential decay of this voltage may be monitored to determine the decay time constant RC. From that time constant and an estimate of the known equivalent capacitance C, the equivalent resistance R presented by the leads may be mathematically estimated. However, this type of measurement may lead to inaccuracies for a number of reasons, including the fact that the discharging of the voltage signal may be affected by other resistances and capacitances in the system, the accuracy of the capacitor, the time, voltage, and algorithmic accuracies of the measurement system, and the like. Also, on occasions, false impedance readings that are not necessarily representative of the true condition of the leads may occur using current methodologies. These false readings may be misinterpreted and an inappropriate action may be performed by the implantable device based upon these false readings. It would be desirable to have a more efficient and accurate method, apparatus, and/or system to measure or assess the health of leads that deliver electrical stimulation or therapy.

The present invention is directed to overcoming, or at least reducing, the effects of, one or more of the problems set forth above.

SUMMARY OF THE INVENTION

In one aspect of the present invention, a method is provided for determining an adverse operational condition associated with a lead assembly in an implantable medical device used for providing a therapeutic electrical signal to a cranial nerve. A first impedance associated with the lead assembly configured to provide the therapeutic electrical signal to a cranial nerve is detected. A determination is made as to whether the first impedance is outside a first predetermined range of values. A second impedance is detected. The detection of the second impedance is performed within a predetermined period of time from the time of the detection of the first impedance. A determination is made as to whether the second impedance is outside a second predetermined range of values. A determination that a lead condition problem exists is made in response to a determination that the first is outside the first predetermined range of values and second impedance is outside the second predetermined range of values. The implantable medical device is prevented from providing the therapeutic electrical signal to the cranial nerve in response to determining that the lead condition problem exists.

In another aspect of the present invention, a method is provided for determining an adverse operational condition associated with a lead assembly in an implantable medical device used for providing a therapeutic electrical signal to a cranial nerve. A first test is performed to determine if a first indication of a lead break is present. A first remedial action is performed based upon a determination that the first indication of a lead break is present. A second test is performed to determine if a second indication of a lead break is present. The second indication of the lead break indicates a significant lead break. A second remedial action is performed based upon a determination that the second indication of a lead break is present. The second remedial action comprises preventing the implantable medical device from applying the therapeutic electrical signal to the cranial nerve.

In yet another aspect of the present invention, an implantable medical device. for determining an adverse operational condition associated with a lead assembly coupled to the implantable medical device. The implantable medical device comprises a stimulation unit to provide a therapeutic electrical signal to a cranial nerve, through a lead operatively coupled to the IMD; an impedance detection unit to provide a first impedance data and a second impedance data; and a controller operatively coupled to the stimulation unit and the impedance detection unit. The controller is adapted to determine that a significant lead condition problem is present in response to a determination that the first and second impedance data are outside a predetermined range of values. The controller is adapted to prevent the stimulation unit from providing the therapeutic electrical signal to the cranial nerve in response to the determination that the significant lead condition problem is present.

In yet another aspect of the present invention, a method is provided for determining a condition associated with a lead assembly in an implantable medical device for providing a therapeutic electrical signal to a cranial nerve. The lead condition of the lead assembly is monitored. Data relating to the lead condition is received. A lead condition analysis is performed to determine whether a lead problem is present. A determination is made as to whether the lead condition is a significant lead condition. The implantable medical device is prevented from providing the therapeutic electrical signal to the cranial nerve upon a determination that the lead condition is a significant lead condition. A secondary operation mode of the implantable medical device is implemented in response to a determination that the lead condition is not a significant lead condition.

BRIEF DESCRIPTION OF THE DRAWINGS

The invention may be understood by reference to the following description taken in conjunction with the accompanying drawings, in which like reference numerals identify like elements, and in which.

Figure 1A:
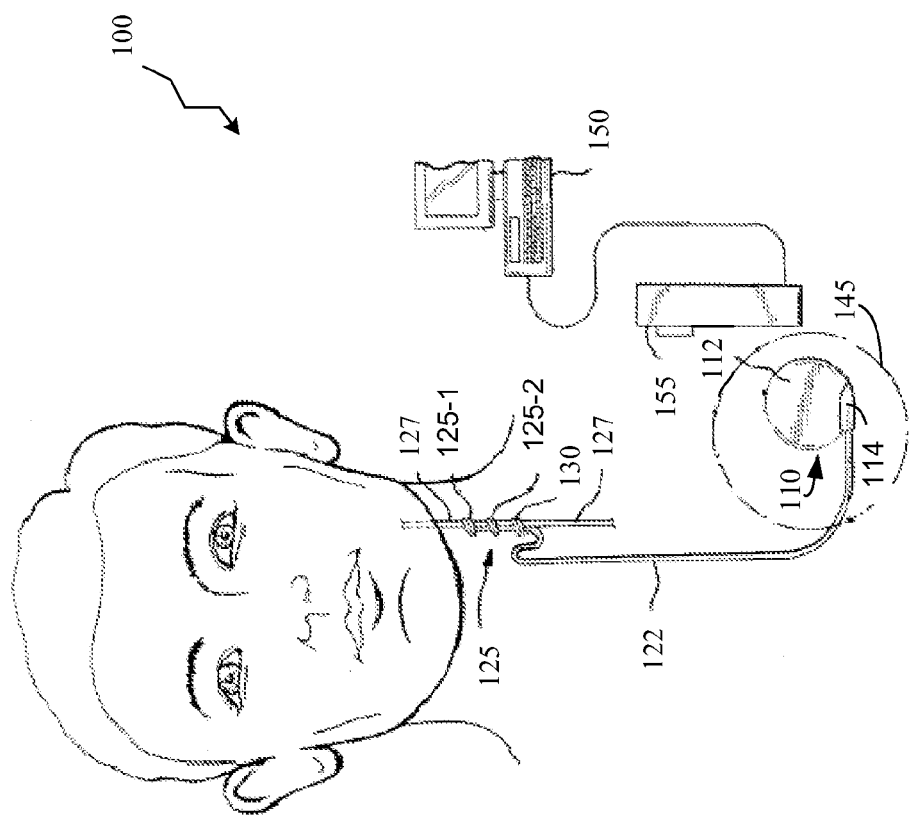
FIGS. 1A-1C are stylized diagrams of an implantable medical device suitable for use in the present invention implanted into a patient's body (FIG. 1A), a detail view of a lead and electrode coupled to a vagus nerve (FIG. 1B), and a front view of an implantable medical device suitable for use in embodiments of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Cranial nerve stimulation has been proposed to treat a number of medical conditions pertaining to or mediated by one or more structures of the nervous system of the body, including epilepsy and other movement disorders, depression, anxiety disorders, bipolar disorder, autism and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult. Moreover, even if such pathways were known, the precise stimulation parameters that would modulate particular pathways relevant to a particular disorder generally cannot be predicted.

Embodiments of the present invention provide for an implantable medical device (IMD) that is capable of monitoring the general state, condition or health of leads coupled to the IMD. The IMD may experience various operational difficulties as a result of problems associated with the lead condition. The lead condition/health may include a break in the lead and/or an electrical short in a conductor coupled to the lead. Problems resulting from the lead condition(s) may include, but are not limited to, a degradation of tissue-matter proximate to the lead, corrosion of the lead, contamination of or damage to the tissue proximate to the lead, pain experienced by a patient, charge imbalance on the IMD electrodes, improper delivery of therapy, etc. Utilizing embodiments of the present invention, the general health/condition of the lead may be monitored and one or more remedial actions may be performed.

An increase or decrease in a controlled current delivered by the IMD, beyond pre-determined tolerance levels may be indicative of unusually high or unusually low lead impedances. Unusually high currents may be indicative of an electrical short associated with the lead. Unusually low currents may be indicative of a lead break. Embodiments of the present invention provide for utilizing a plurality of measurements of parameters potentially indicative of problem(s) associated with the lead, and to take at least one remedial action. For example, a plurality of lead impedance measurements may be made to determine whether the health/condition of a lead has been compromised. Acquiring a plurality of measurements upon which to assess lead condition/health reduces the possibility of a false indication of a lead condition problem. Further, multiple lead parameter measurements may shed light upon an during certain time periods or certain positions of the patient's body. For example, intermittent lead problems may occur in some cases only when the patient's body is in a particular position, such as a position of overly extended arms. If reliance on a single measurement is made, an over-reaction to an intermittent lead problem may occur, or in other cases the problem may not be detected at all. The present invention provides for a reduction in this potential overreaction.

On the other hand, if a severe lead health/condition is detected, the severity of this problem may be verified by multiple measurements of parameters indicative of a lead condition problem, and any of a range of appropriate remedial actions may then be taken. Embodiments of the present invention provide for utilizing a plurality of types of measurements, such as lead impedance measurements, charge imbalance measurements, low current measurements, high current measurements, power output measurements, energy output measurements, charge delivered per pulse measurements, "make-up" voltage measurements, etc., to detect possible problems in lead health. Further, one or more of these parameters may be measured multiple times to better identify the severity and frequency of the lead condition problem. For example, lead problems may be categorized into groups, such as 1) rare intermittent problems, 2) frequent intermittent problems, 3) constant lead problems, etc., and may be identified based upon the measurements described herein. Reactions to a lead condition problem may be based upon these categorizations. Further, the measurements may be repeated at pre-determined intervals and numbers to ensure reliable and accurate assessment of the lead health. Statistical analyses may be performed based upon the frequency of lead problems, severity of the lead problems, the type of measurements indicative of lead problems, etc., which may shed light as to the actual lead condition/health.

Based upon the assessment of the lead health, various actions may be provided by embodiments of the present invention. This may include performing one or more actions selected from a range of actions, wherein the least severe action in the range may be ignoring intermittent problems, and the most severe may be a full scale shut down of operations of the IMD, which may include notifying the patient, physician, and/or manufacturer of the condition. Other steps, such as reduction in one or more electrical parameters defining the therapeutic electrical signal delivered by the IMD, may also be performed as a remedial action. Other remedial actions may include reducing the frequency of delivery of the therapeutic electrical signal, and/or performing a pre-stimulation assessment of the lead condition prior to delivery of the therapeutic electrical signal to ensure that the health of the lead is acceptable and capable of delivering the signal to the target tissue. In this manner, intermittent problems, such as lead breaks occurring when a patient is in a certain position (e.g., reclining, turning the head, raising an arm), may be bypassed by rescheduling delivery of therapy until a later pre-stimulation assessment operation ensures that the current lead health is acceptable.

Figure 1C:
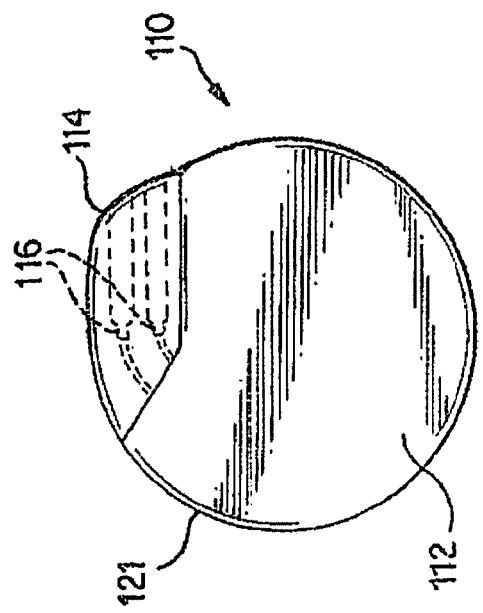
Figure 1B:
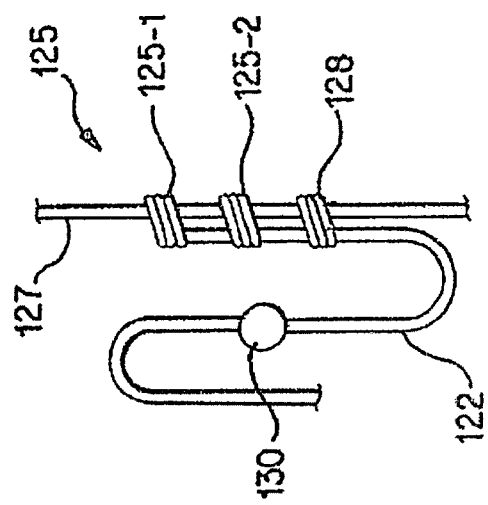

Turning now to FIGS. 1A-1C, stylized diagrams are provided of an implantable medical device implanted into a patient's body for providing electrical stimulation to a portion of the patient's body, in accordance with one illustrative embodiment of the present invention. FIGS. 1A-1C depict a stylized implantable medical system 100 for implementing one or more embodiments of the present invention. FIGS. 1A-1C illustrate an electrical signal generator 110 having a main body 112 comprising a case or shell 121 with a header 114 (FIG. 1C) for connecting to at least one lead 122. The electrical signal generator 110 is implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125 (FIG. 1B) is conductively coupled to the distal end of an insulated, electrically conductive lead assembly 122, which preferably comprises one wire for each electrode of the electrode assembly 125. Lead assembly 122 is conductively coupled at its proximal end to connectors on the header 114 on case 121. The electrode assembly 125 may be surgically coupled to a vagus nerve 127 in the patient's neck (FIGS. 1A, 1B) or at another location, e.g., near the patient's diaphragm (not shown). The electrical signal may also be applied to other cranial nerves, e.g., the trigeminal or glossopharyngeal nerves. The electrode assembly 125 is preferably wrapped around the vagus nerve, and the electrode assembly 125 may be secured to the nerve 127 by a spiral anchoring tether 128 (FIG. 1B) such as that disclosed in U.S. Pat. No. 4,979,511 issued Dec. 25, 1990 to Reese S. Terry, Jr. and assigned to the same assignee as the instant application. Lead assembly 122 can be secured, while retaining the ability to flex with movement of the chest and neck, by a suture connection 130 to nearby tissue (FIG. 1B).

In one embodiment, the electrode assembly 125 has an open helical design, which is self-sizing and flexible to minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises at least one ribbon electrode, of a conductive material such as platinum, iridium, platinum-iridium alloys, or oxides of the foregoing.

In one embodiment, the IMD is used to perform active stimulation in response to an input received by the IMD from a sensor. Other embodiments of the present invention use passive stimulation to deliver a continuous, periodic, or intermittent electrical signal to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical signal generator 110 may be programmed with an external computer 150 using programming software of the type copyrighted by the assignee of the instant application with the Register of Copyrights, Library of Congress, or other suitable software based on the description herein. In one embodiment, a programming wand 155 can be used to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator. In an embodiment using RF frequencies in the Medical Implants Communications Service (MICS) bands, the wand 155 may be omitted.

By providing the therapeutic electrical signal, the electrical signal generator 110 may treat a disorder or a medical condition of a patient. A generally suitable form of neurostimulator for use in the method and apparatus of the present invention is disclosed, for example, in U.S. Pat. No. 5,154,172, assigned to the same assignee as the present application. A commercially available example of such a neurostimulator is available from Cyberonics, Inc., Houston, Tex., the assignee of the present application. Certain parameters defining the therapeutic electrical signal generated by the electrical signal generator 110 are programmable, such as by means of an external programmer in a manner conventional for implantable electrical medical devices.

Figure 2:
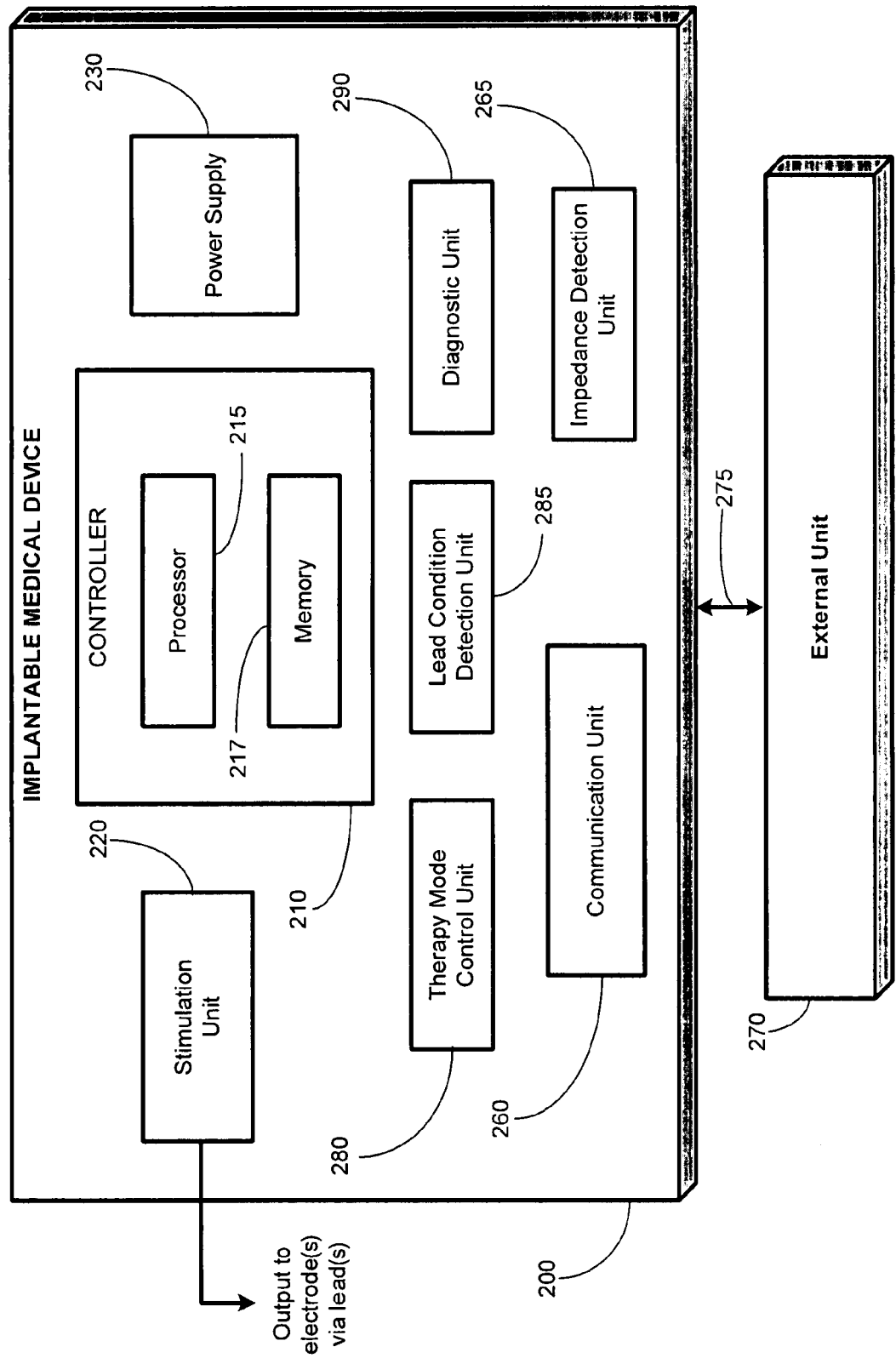
FIG. 2 is a block diagram of an implantable medical device and an external unit that communicates with the implantable medical device, in accordance with one illustrative embodiment of the present invention.

Turning now to FIG. 2, a block diagram depiction of an implantable medical device (IMD), in accordance with one illustrative embodiment of the present invention is illustrated. The IMD 200 may be used for stimulation to treat various disorders, such as epilepsy, depression, bulimia, traumatic brain injury, heart rhythm disorders, etc. The IMD 200 may be coupled to various electrodes associated with the leads 122 (FIG. 1A). Therapeutic electrical signals may be transmitted from the IMD 200 to target areas of the patient's body, specifically to various electrodes associated with the leads 122. Therapeutic electrical signals from the IMD 200 may be transmitted via the leads 122 to stimulation electrodes associated with the electrode assembly 125 (FIG. 1B). Further, signals from sensor electrodes, e.g., 125 (FIG. 1A) associated with corresponding leads may also traverse the leads back to the IMD 200.

Referring again to FIG. 2, the implantable medical device 200 may comprise a controller 210 capable of controlling various aspects of the operation of the IMD 200. The controller 210 is capable of receiving internal data and/or external data and generating and delivering a stimulation signal to target tissues of the patient's body. For example, the controller 210 may receive manual instructions from an operator externally, or may perform stimulation based on internal calculations and programming. The controller 210 is capable of affecting substantially all functions of the IMD 200. The controller 210 is capable of detecting various lead health parameters and performing a lead health analysis. Further, the controller is capable of performing one or more remedial actions based upon an assessment of the lead health, which are further described herein.

The controller 210 may comprise various components, such as a processor 215, a memory 217, etc. The processor 215 may comprise one or more microcontrollers, microprocessors, etc., that are capable of performing various executions of software components. The memory 217 may comprise various memory portions where a number of types of data (e.g., internal data, external data instructions, software codes, status data, diagnostic data, etc.) may be stored. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering stimulation signals to one or more electrodes via leads. A number of leads 122 may be coupled to the IMD 200. Therapy may be delivered to the leads 122 by the stimulation unit 220 based upon instructions from the controller 210. The stimulation unit 220 may comprise various circuitry, such as stimulation signal generators, impedance control circuitry to control the impedance "seen" by the leads, and other circuitry that receives instructions relating to the type of stimulation to be performed. The stimulation unit 220 is capable of delivering a controlled current stimulation signal to a target tissue over the leads 122 via one or more electrodes 125. A more detailed illustration of the stimulation unit 220 is provided in FIG. 3 and accompanying description below.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride cell (LiCFx). Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 is a computer system that is capable of executing a data-acquisition program. The external unit 270 may be controlled by a healthcare provider, such as a physician, at a base station, for example, in a doctor's office. The external unit 270 may be a computer, preferably a handheld computer or PDA, but may alternatively comprise any other device that is capable of electronic communications and programming, e.g., a programmable cellphone. The external unit 270 may download various parameters and program software into the IMD 200 for programming the operation of the implantable medical device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

The IMD 200 may also comprise diagnostic unit 290, a therapy mode control unit 280, a lead condition detection unit 285, and an impedance detection unit 265. The diagnostic unit 290 may provide for performing various diagnostics, such as lead impedance tests, tests associated with the stimulation signals, system diagnostic tests, etc., which are described in further detail below. Upon receiving instructions from the external unit 270, the IMD 200 may perform various diagnostics tests as directed by the diagnostics unit 290 and the controller 210. In one embodiment, examples of the lead impedance test may include verifying the impedance of the lead to determine whether there is a problem in the electrical path defined by the path from the IMD 200, through the leads, through the electrodes, and onto the portion of the patient's body targeted for stimulation. Further tests performed by the diagnostic unit 290 may include verifying automatic capture of various patient data, verifying proper reception of data via sensing electrodes, verifying endogenous nerve activity (i.e., electrical activity naturally occurring in the nerve, independent of the therapeutic electrical signal), verifying the integrity and characteristics of the therapeutic electrical signal, verifying whether particular portions of a nerve (e.g., the A-fiber, the B-fibers and/or the C-fiber) are being adequately targeted. This determination may be made by examining the data detected by one or more sensors, (e.g., a sensor electrode in communication with the IMD 200).

The impedance detection unit 265 is capable of acquiring impedance data relating to leads coupled to the IMD 200. The impedance detection unit 265 is capable of performing measurements at pre-determined intervals, or upon a command from the controller 210. A more detailed illustration of the impedance detection unit 265 is provided in FIG. 4 and the accompanying description below.

The lead condition detection unit 285 is capable of assessing the health or condition of the lead(s) coupled to the IMD 200 based upon various parameters, e.g., data from the lead detection unit 265 and/or the diagnostic unit 290. Based upon the condition of the lead, a determination is made as to whether the lead problem is a constant or permanent problem, or an intermittent problem. The lead condition detection unit 285, in one embodiment, is capable of determining the severity and the type of permanent or intermittent lead problem that may be detected. Further, in one embodiment, the lead condition detection unit 285 may perform a ranking type function, ranking the degree of the severity of the lead health (e.g., ranking an error as a rare and serious intermittent error, a frequent and major intermittent error, or a constant and minor error. Further description of detecting the lead condition performed by the lead condition detection unit 285 is provided below.

Based upon the assessment performed by the lead condition detection unit 285, the therapy mode control unit 280 may control the operations performed by the stimulation unit 220. The therapy mode control unit 280 may define the stimulation pulses to be delivered to the nerve tissue according to parameters and waveforms that may be programmed into the IMD 200 using the external unit 270. The therapy mode control unit 280 controls the operation of the stimulation unit 220, which generates the stimulation pulses according to the parameters defined by the controller 230; and in one embodiment, provides these pulses to the connector 116 for delivery to the patient via lead assembly 122 and electrode assembly 125 (see FIGS. 1A-1C). Various stimulation signals provided by the implantable medical device 200 may vary widely across a range of parameters.

The therapy mode control unit 280 is capable of controlling the mode in which the IMD 200 operates based upon data from the lead condition detection unit 285. Based upon the type of lead health/condition detected, the therapy mode control unit 280 may cause a change in the operation mode of the IMD 200. For example, upon detection of a serious and/or constant lead health error (e.g., a constant lead short or a lead break), the therapy mode control unit 280 may simply prevent further delivery of therapeutic electrical signals until further evaluation and/or adjustments of the leads are performed.

In instances where an intermittent lead condition problem is detected, the therapy mode control unit 280 may prompt the IMD 200 to enter an alternative/secondary operation mode (as opposed to a normal operation mode when no lead condition problems are detected). The alternative/secondary operation mode of the IMD 200 may take on various forms of modified delivery of stimulation signals, such as a reduction in the energy output provided by the stimulation electrical signal. Further, other implementations of a secondary operation, such as a pre-stimulation operation check mode may be implemented. The pre-stimulation operation mode may include performing an assessment of the lead health immediately prior to delivery of a therapeutic electrical signal burst. The pre-stimulation assessment may include a pre-determined set of diagnostic-type tests that may be performed substantially immediately before the delivery of a therapeutic electrical signal. The therapy mode control unit 280 is capable of controlling the output provided by the stimulation unit 220. Other operational modifications, such as turning off a particular lead, may also be performed. In this manner, a different type of stimulation that includes a different of electrode usage for delivery of therapy may be provided. Further, other reactions, such as utilizing a uni-polar delivery of the therapeutical electrical signal, instead of a more conventional bipolar delivery, may be implemented. The uni-polar mode may include delivery of a stimulation signal via a single lead, wherein the electrical reference points (anode and cathode) are the lead tip and the case or shell 121 of the IMD 200.

Further, embodiments of the present invention provide for a notification function to be performed upon detection of adverse lead conditions. For example, notification to the patient may be performed upon detection of a lead health issue. Other notifications, such as logging the error, communicating the error to a healthcare professional (e.g., the physician), alerting the manufacturer of one or more components associated with the IMD 200, etc., may be performed. These notifications may then be utilized by the recipient to implement changes, such as surgical adjustment of the leads, adjustment of the therapeutic electrical signal delivery, modification to the IMD or related equipment, etc. The communication unit 260 is capable of performing the notification described above. The communication unit 260 may comprise a variety of types of communication interfaces that are capable of providing instant notification to the patient, the physician, the manufacturer, etc. The electronic communication means may be comprised within the communication unit 260 that provide for communication via the internet to the various targeted recipients of the notification described herein.

It will be recognized that one or more of the blocks 210-290 of FIG. 2 (which may also be referred to as modules) may comprise hardware, firmware, software, or any combination thereof. Additionally, one or more functions associated with blocks illustrated in FIG. 2 may be combined with those of other blocks, which may represent circuit hardware units, software algorithms, etc. Some of these modules may reside or may be merged into the controller 210. Additionally, any number of the circuitry or software units associated with the various blocks illustrated in FIG. 2 may be combined into a programmable device, such as a field programmable gate array, an ASIC device, etc.

Figure 3:
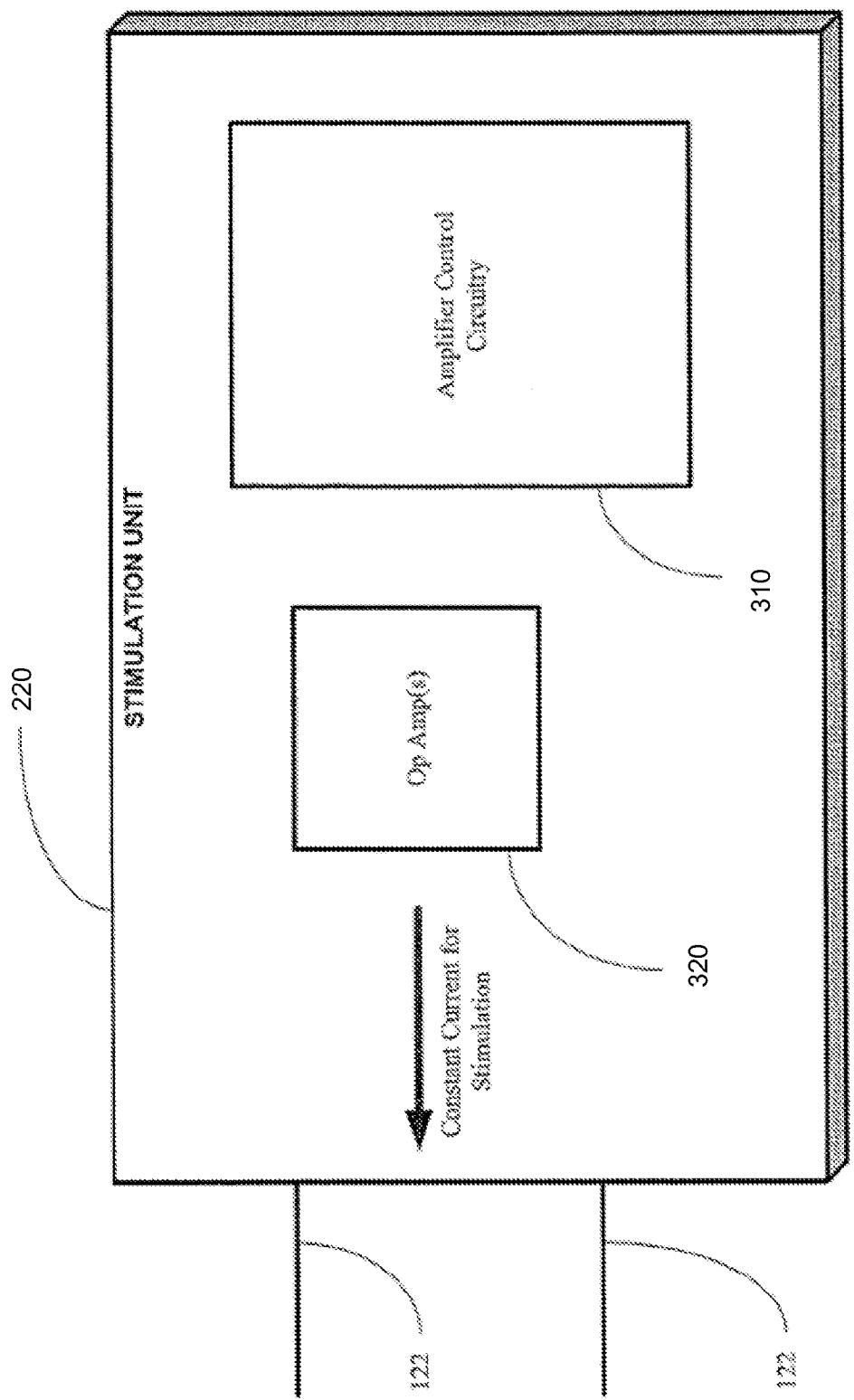
FIG. 3 provides a more detailed block diagram depiction of a stimulation unit of FIG. 2, in accordance with one illustrative embodiment of the present invention.

Turning now to FIG. 3, further details of a block-diagram depiction of one embodiment of the stimulation unit 220 of FIG. 2, if provided. The stimulation unit 220 of the IMD 200 comprises an op amp unit 320, which may comprise one or more operational amplifiers that are capable of delivering a controlled current therapeutic electrical signal for stimulation. In one embodiment, the controlled current is a constant current or a substantially constant current. The stimulation unit 220 may also comprise an amplifier control circuitry unit 310 that may contain circuitry and/or programmable logic to control the operation of the op amps 320. Additionally, the stimulation unit 220 may be coupled to leads 122, which may comprise a pair of signal wires capable of delivering an electrical signal to an electrode pair 125-1 and 125-2 (FIG. 1B) each coupled to a distal end of one of the leads 122. The leads 122 (and the electrodes 125-1 and 125-2) are capable of providing a complete circuit between the implantable medical device 200 and the region of the body/tissue to which the electrodes are attached, which may be approximated as an equivalent impedance. Each lead 122 may comprise a single strand wire or, more preferably, a multi-strand wire braided or otherwise coupled together as a single functional wire. Each of the two lead wires 122 in this embodiment is provided with a separate socket and connector 116, as shown in FIG. 1C. In another embodiment, two leads 122 may be combined into a single coaxial cable (as shown in FIGS. 1A and 1B), with a single socket providing both coaxial connectors 116.

Embodiments of the present invention provide for utilizing the delivery of a constant current signal for delivery of a therapeutic electrical signal, and measurement of the impedance experienced by the leads 122. In a preferred embodiment, the controlled or constant current signal provided by the stimulation unit 220 is independent of the impedance experienced across the leads 122. For example, even if the impedance experienced across the leads 122 changes, the op amp 320, in conjunction with the amplifier control circuitry 310, adjusts to deliver a controlled or constant current despite the change in the impedance experienced across the leads 122.

Since a controlled, constant current is delivered despite variations in the impedance across the leads 122, the voltage across the lead terminals can be used to provide an indication of the lead impedance. For example, if the nerve tissue to which the leads 122 are connected has an impedance of 1000 ohms, a particular stimulation may call for a one milliamp constant current signal. In this case, even if a 5000 ohms impedance is experienced across the leads 122, the stimulation unit 220 will still provide a one milliamp current. Hence, the power may vary but the current remains constant. In other words, the op amp 320 will stabilize itself utilizing various circuitry, including the amplifier control circuitry 310, to provide a constant current signal even if the impedance experienced by the leads 122 varies during the period the signal is provided. Therefore, using Ohm's Law, V=IR, a measurement of the voltage across the leads 122 will provide an indication of the actual impedance experienced by the leads 122.

Figure 4:
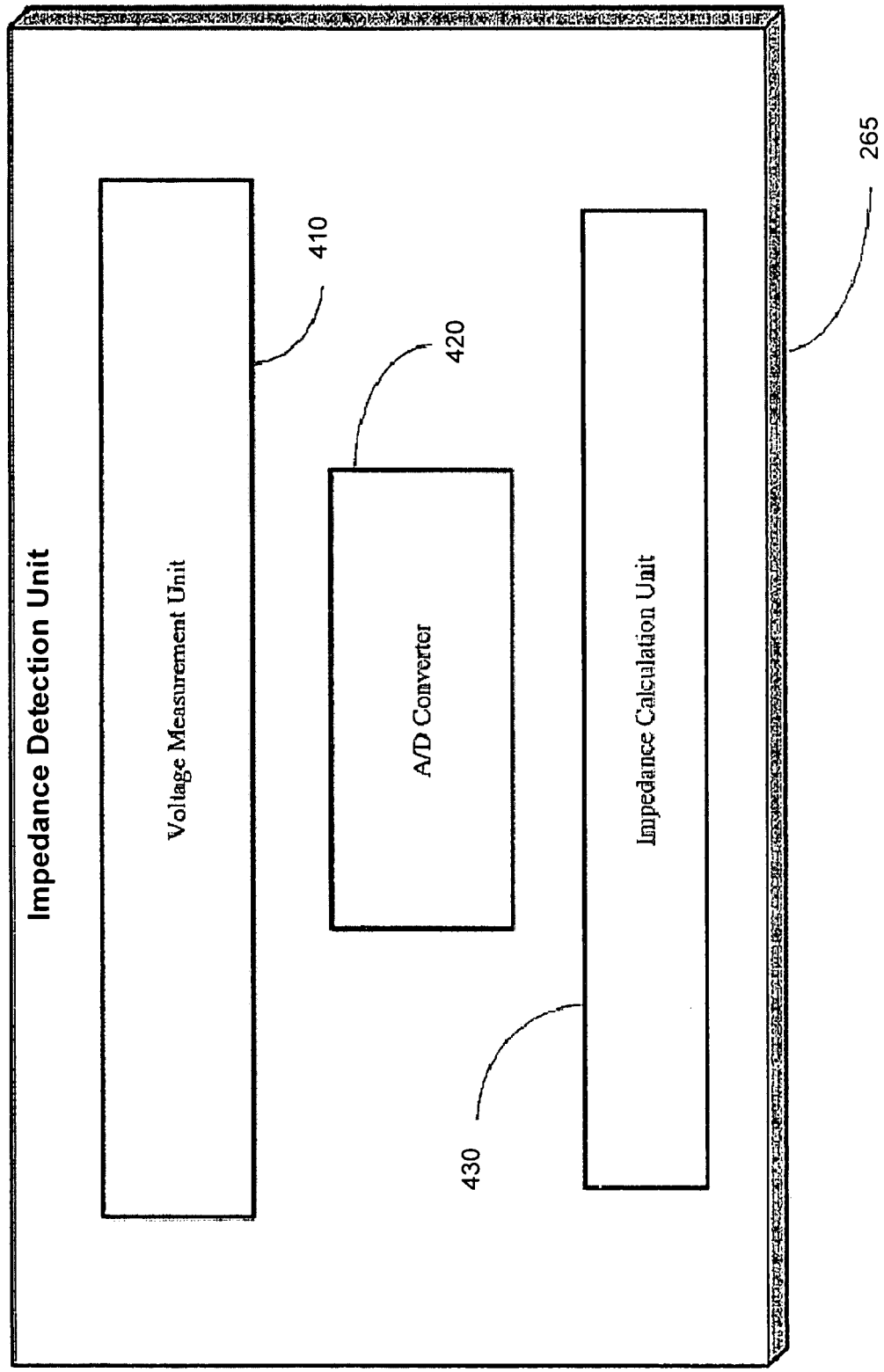
FIG. 4 illustrates a block diagram depiction of an impedance detection unit of FIG. 2, in accordance with one illustrative embodiment of the present invention.

Turning now to FIG. 4, a block diagram depiction of one embodiment of the impedance detection unit 265 from FIG. 2 is provided. In one embodiment, the impedance detection unit 265 comprises a voltage measurement unit 410, an A/D converter (analog to digital converter) 420 and an impedance calculation unit 430. The voltage measurement unit 410 is capable of measuring or determining the voltage differential between the terminals of the leads 122. The signal from the voltage measurement unit 410 is generally an analog signal, which may be sent to the A/D converter 420. The A/D converter 420, which preferably has been calibrated prior to the operation of the IMD 200, will convert the analog voltage measurement signal to a digital signal. In alternative embodiments of the present invention the impedance detection unit 265 may be implemented without the use of the A/D converter 420 and still remain within the scope of the present invention.

Although certain embodiments may be implemented without it, the A/D converter 420 may be beneficial for enhancing the resolution of the voltage signal, thereby providing for enhanced analysis of the voltage across the leads 122. Based upon the voltage across the leads 122, and the constant current signal provided by the stimulation unit 220, the impedance calculation unit 430 calculates the impedance by dividing the voltage across the lead terminals 122 by the current delivered by the stimulation unit 220. The impedance calculation unit 430 may be a hardware unit, a software unit, a firmware unit, or any combination thereof, which may be located in various portions of the IMD 200, including in the impedance detection unit 265, in the stimulation controller 230, in the power source controller 220, or in any other portion of the IMD 200.

In an alternative embodiment, the calculation described as being performed by the impedance calculation unit 430 may alternatively be performed by the external unit 270, which may receive the signal relating to the constant current stimulation signal and the measured voltage signal. One of the advantages of utilizing the embodiments provided by the present invention is that substantially any size of a constant or controlled current stimulus signal may be used to perform the impedance measurement, thereby conserving battery power of the implantable medical device 200. Accordingly, the smallest stimulation signal that may reliably be provided by the stimulation unit 220 may be used to perform the impedance measurement. Thus, the impedance measurement may be made without imposing a significant charge depletion burden on the battery. Additionally, the impedance of the leads 122 themselves is also accounted for when analyzing the impedance. Furthermore, the A/D converter 420 may be calibrated prior to the operation of the implantable medical device 200, for example, during the manufacturing process.

Turning again to FIGS. 1A and 1B, the leads 122 are shown connected to tissue (e.g., nerve tissue 127) in a patient's body and to the IMD 200. The implantable medical device 200 may comprise a main body 112 (FIG. 1A) in which the electronics described in FIG. 2 are enclosed. Coupled to the main body 112 is a header 114 designed with terminal connectors 116 (FIG. 1C) for connecting to leads 122. The main body 112 may comprise a titanium case 121 and the header 114 may comprise a biocompatible polymer such as polyurethane or acrylic. The leads 122 projecting from the header 114 may be attached to the tissue utilizing a variety of methods for attaching the leads 122 to tissue. A first end of the leads 122 is coupled to connector(s) 116 on the header 114, and a distal end is coupled to the tissue by electrodes 125-1 and 125-2, which together provide a cathode and an anode (FIG. 1C). Therefore, the current flow may take place from one electrode 125-1 to a second electrode 125-2 via the tissue, thereby delivering the stimulation.

The system illustrated in FIGS. 1A-1C may be viewed as an electrical circuit that includes a current or voltage source (i.e., the power source 230 of the IMD 200) being connected to an impedance (i.e., the equivalent impedance of the tissue) via a pair of wires (i.e., the leads 122). The total impedance connected to the IMD 200 includes the impedance of the lead wires 122 as well as the impedance across the terminals 116 of the leads 122 to the tissue. One of the biggest components of the impedance experienced by terminals 116 on the header 114, to which the leads 122 are connected, is the impedance of the tissue. Therefore, if a break in any one portion of the lead wires 122 occurs (such as a break in one or more strands of a multistrand wire), the impedance may rise significantly, which may provide an indication that a break in the lead wire 122 has occurred. Conversely, if a short is in the lead wires 122 occurs, the impedance may drop significantly.

Figure 5:
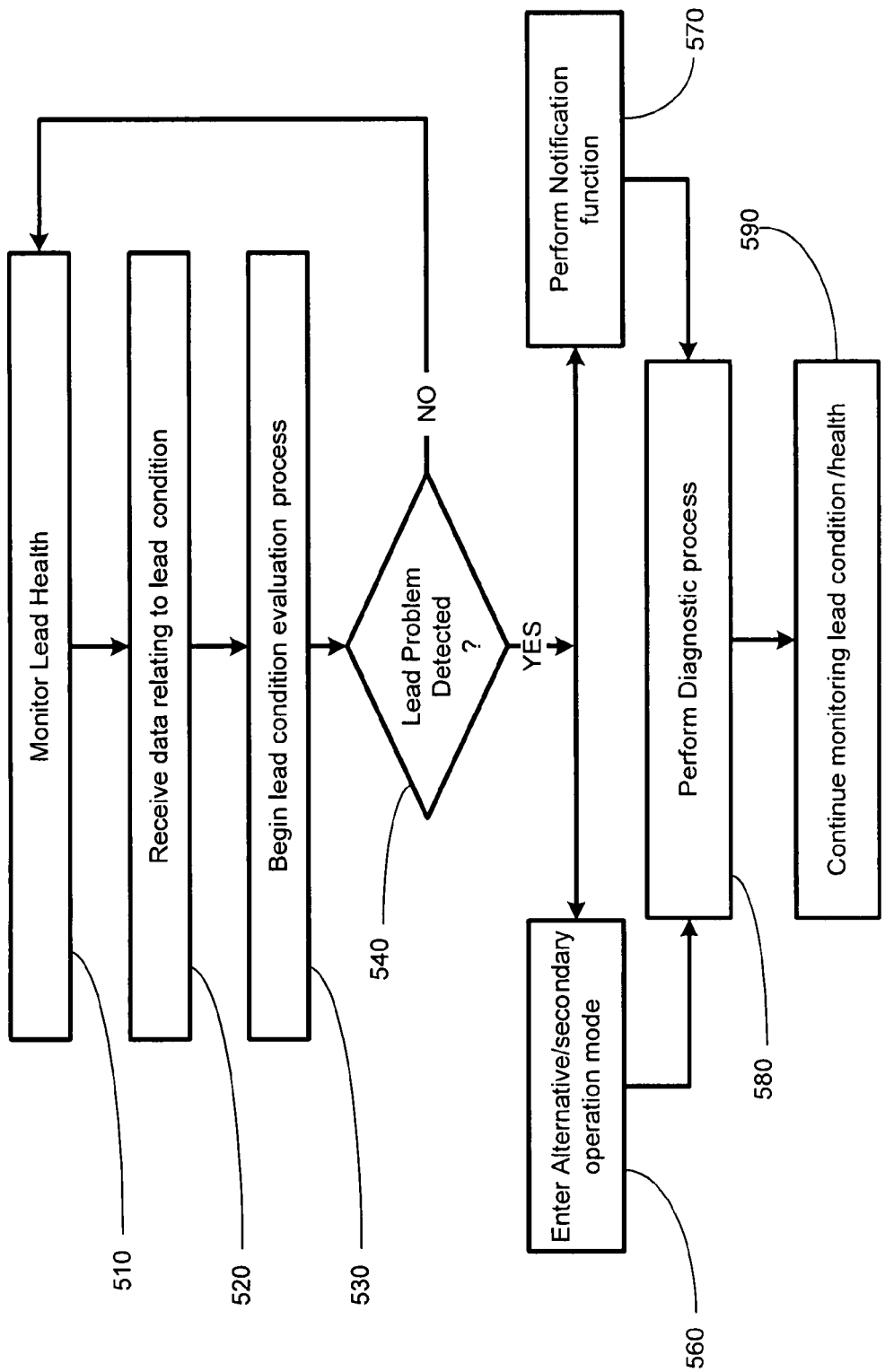
FIG. 5 illustrates a flow chart depiction of a method of monitoring and responding to a lead health determination, in accordance with one illustrative embodiment of the present invention.

Turning now to FIG. 5, a flowchart depiction of the method associated with monitoring the lead health in accordance with one illustrative embodiment of the present invention is provided. The IMD 200 may perform the operation of monitoring of the lead health/condition (block 510). Monitoring the lead health/condition may include performing tests for detecting lead impedances and/or other parameters that may be indicative of a lead break or an electrical short of a conductor associated with the lead. The monitoring of the lead health may be performed at predetermined intervals, or by a user such as a physician prompting the IMD 200 to perform such an assessment, which may be communicated to the external unit 270 via the communication unit 260 (FIG. 2).

Upon implementing the step of monitoring of the lead condition, the IMD 200 may receive data relating to the lead condition (block 520). This data may include various parameters that may be associated with the condition of the lead. These parameters, for example, may include data relating to low current, high current, lead impedance, power output, energy output, charge delivered per pulse, charge imbalance, "make-up" voltage, experienced by the IMD 200. The "make-up" voltage refers to the boost in voltage or current provided by the IMD 200 in response to detecting a reduction of voltage across the electrodes associated with the leads. For example, if a lead break is present, the IMD 200 may attempt to provide a boost in the voltage and/or current to compensate for any potential loss of energy in order to provide predetermined therapeutic signals. Embodiments of the present invention may also be implemented by examining other parameters that may be assessed by those skilled in the art having benefit of the present invention. Upon receiving the data relating to the lead condition or health, the IMD 200 may begin a lead condition evaluation process (block 530). The lead condition/health evaluation process may include various steps to determine whether a lead health problem indeed exists. Further details relating to the lead health evaluation process of FIG. 5 are provided in FIGS. 6 and 7 and accompanying text.

After performing the lead condition evaluation process 530, the IMD 200 may next determine whether a lead health problem is detected (block 540). If the IMD 200 determines that a lead condition/health problem is not detected, the IMD 200 may choose to continue monitoring the lead condition based upon pre-determined programming. On the other hand, if a lead condition problem is detected, the IMD 200 may perform a notification function (block 570). Various entities, such as the patient, a healthcare professional, a manufacturer of one or more components of the IMD system, etc., may be notified. This notification may also include storing of markers or "flags" that may be detected at a later time or in real time. Further, other notifications, such as an email, electronics communications, alarms, etc., may be performed.

Additionally, upon detecting a lead health problem, the IMD 200 may enter an alternative/secondary operation mode (block 560). The alternative/secondary operation mode may allow the IMD to continue to provide continuous therapeutic operation, but in a different mode as to reduce the possibility of damage caused by any particular lead problem. Further, avoiding delivery of therapy during problematic periods where intermittent problems may be detected is also made possible by the alternative/secondary operation mode. Upon entering such a alternative/secondary operation mode, the IMD 200 may perform a diagnostic process (block 580) to determine if there are any further problems associated with the lead health (block 590), or with other aspects of the IMD such as the battery. A more detailed description of entering the alternative/secondary operation mode is provided in FIG. 8 and accompanying description below. Further, a more detailed illustration of performing the notification function of block 570 is provided in FIG. 9 and accompanying description.

Figure 6:
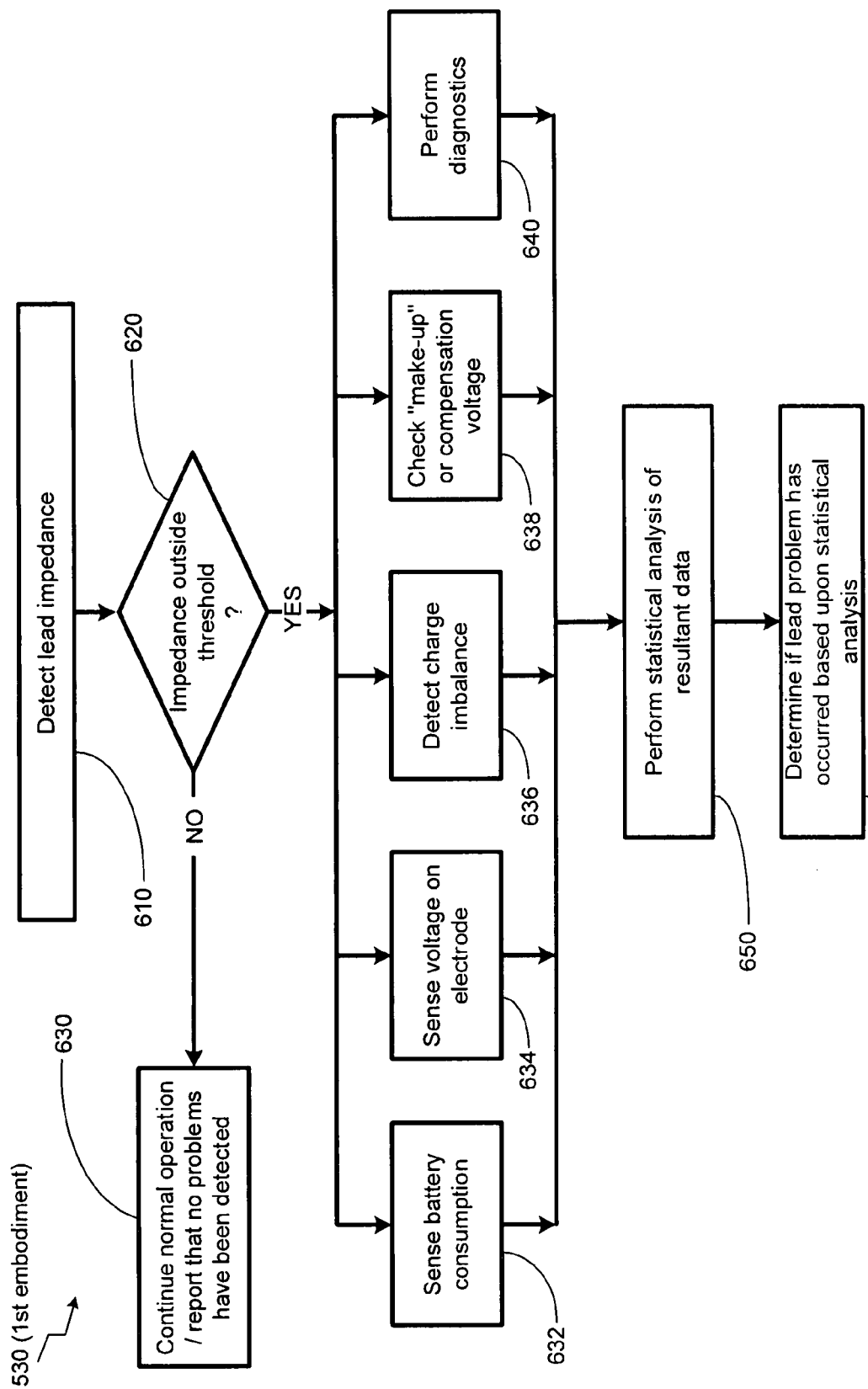
FIG. 6 illustrates a flow chart depiction of a first embodiment of performing a lead condition evaluation process of FIG. 5, in accordance with one illustrative embodiment of the present invention.

Turning now to FIG. 6, a first flowchart depiction of performing a lead condition/health evaluation process of block 530 of FIG. 5, in accordance with a first embodiment of the present invention, is provided. In one embodiment, the lead health evaluation process may include determining a lead impedance 610. In one embodiment, a substantially high lead impedance that is above a predetermined threshold or level of tolerance may signify a lead break. Similarly, a substantially low impedance that is below a predetermined threshold or level of tolerance may signify an electrical short. The various tolerances and thresholds discussed herein would be understood by those skilled in the art having benefit of the present disclosure.

Stimulation is delivered by the IMD 200 to the tissue of the patient by any one of a number of available stimulation delivery modes, such as a constant current signal pulse. To conserve battery power, impedance may be determined using a small magnitude and/or short duration test pulse. The resultant voltage induced across the leads 122 is measured upon delivery of the test pulse. Voltage measurement may be performed by the voltage measurement unit 410 (FIG. 4) during delivery of the test pulse. The IMD 200 adjusts the time at which the voltage is measured such that it occurs while the test pulse is being delivered.

An analog-to-digital (A/D) conversion is preferably performed on the voltage signal measured during the test pulse. Although embodiments of the present invention may be performed without utilizing an A/D converter 420, in one embodiment, an A/D converter 420 (FIG. 4) is used to provide precise resolution of the voltage signal. The A/D converter 420 is preferably calibrated prior to the conversion of the voltage signal from analog to digital. Finally, the impedance is calculated utilizing the amplitude of the current delivered for stimulation and the corresponding voltage measurement. The voltage measured during the test pulse is divided by the value of the current to arrive at the total impedance across the terminals 116 of the header 114 (FIG. 1C). In one embodiment, the predetermined impedance of the lead 122 itself may be subtracted to arrive at the impedance across the lead terminals 116, which corresponds to the impedance of the tissue. Various operational adjustments to the operation of the IMD 200 may be made based upon the determination of the impedance across the terminals 116.

Once the lead impedance is determined (block 610), the IMD 200 may determine whether the impedance is outside an acceptable, predetermined threshold or level of tolerance (block 620). Upon a determination that the impedance is not outside a threshold level, or is within an acceptable range of tolerance, the IMD 200 may continue normal operation and/or report that no lead condition problems have been detected (block 630). If the IMD 200 determines that the lead impedance is outside the threshold value, then various steps illustrated in FIG. 6 may be performed. In order to determine whether the impedance is outside the threshold values, the IMD 200 may repeat the detection of the lead impedance a number of times. For example, three consecutive high impedance indications within a predetermined period of time may be interpreted as a high impedance problem that would be unacceptable. Various time periods for performing consecutive high impedance measurements may be programmed, such as a first time-interval of three days, a second time-interval of a few minutes, or shorter periods associated with body movements, such as a few seconds, etc. Historical records relating to a particular IMD 200, or a particular patient, may be used to determine what type of intervals may be necessary in order to verify that an acceptable lead impedance situation has indeed occurred.

Upon a determination that the impedance is outside the acceptable threshold, the IMD 200 may determine one or more parameters such as battery consumption or remaining battery life (block 632), voltage on the electrode (block 634), charge imbalance (block 636), make-up or compensation voltage (block 638), and/or perform various diagnostics tests (block 640). In other words, the detection of an unacceptable impedance may be combined with one or more other parameters associated with the operation of the IMD 200 to determine whether a lead health problem indeed exists. For example, a charge imbalance, in combination with the existence of a lead impedance problem, may be indicative that a lead condition problem indeed exists.

One embodiment of performing the charge imbalance detection step may include detecting voltages on electrodes during "off time," when no signal is being applied to the target tissue. The voltages may be examined in a differential fashion, wherein, if different voltages on each electrode exist, this may be indicative of a charge imbalance. The make-up or compensation voltage of block 638 may refer to a boost in the voltage provided by the IMD 200 to compensate for any loss of energy. A voltage boost signal ("$V_{boost}$") may be provided by the IMD 200 to increase the amount of energy to ensure that predetermined levels of energy in the therapeutic electrical signal (or the test pulse) is delivered. However, in situations such as a lead break, the attempt to compensate by increasing the $V_{boost}$ signal may not suffice and desired levels of energy delivery may not take place at all.

Based upon the detection of various parameters described above, as well as the lead impedance, the IMD 200 may perform a statistical analysis of the resultant data (block 650). This analysis may include analyzing one or more of the parameters described above (e.g., battery consumption/life, electrode voltage, charge imbalance, makeup voltage, etc.) to determine if one or more parameters enter an unacceptable range of values within predetermined time periods and/or predetermined frequency. For example, a determination is made whether a combination of one or more parameters described above enters an unacceptable range of values three times during a predetermined time frame. Other statistical analysis techniques may be used to determine whether a significant lead health issue exists. Upon performing the statistical analysis, the IMD 200 may determine if a lead problem has indeed occurred based upon the statistical analysis (block 660).

Figure 7:
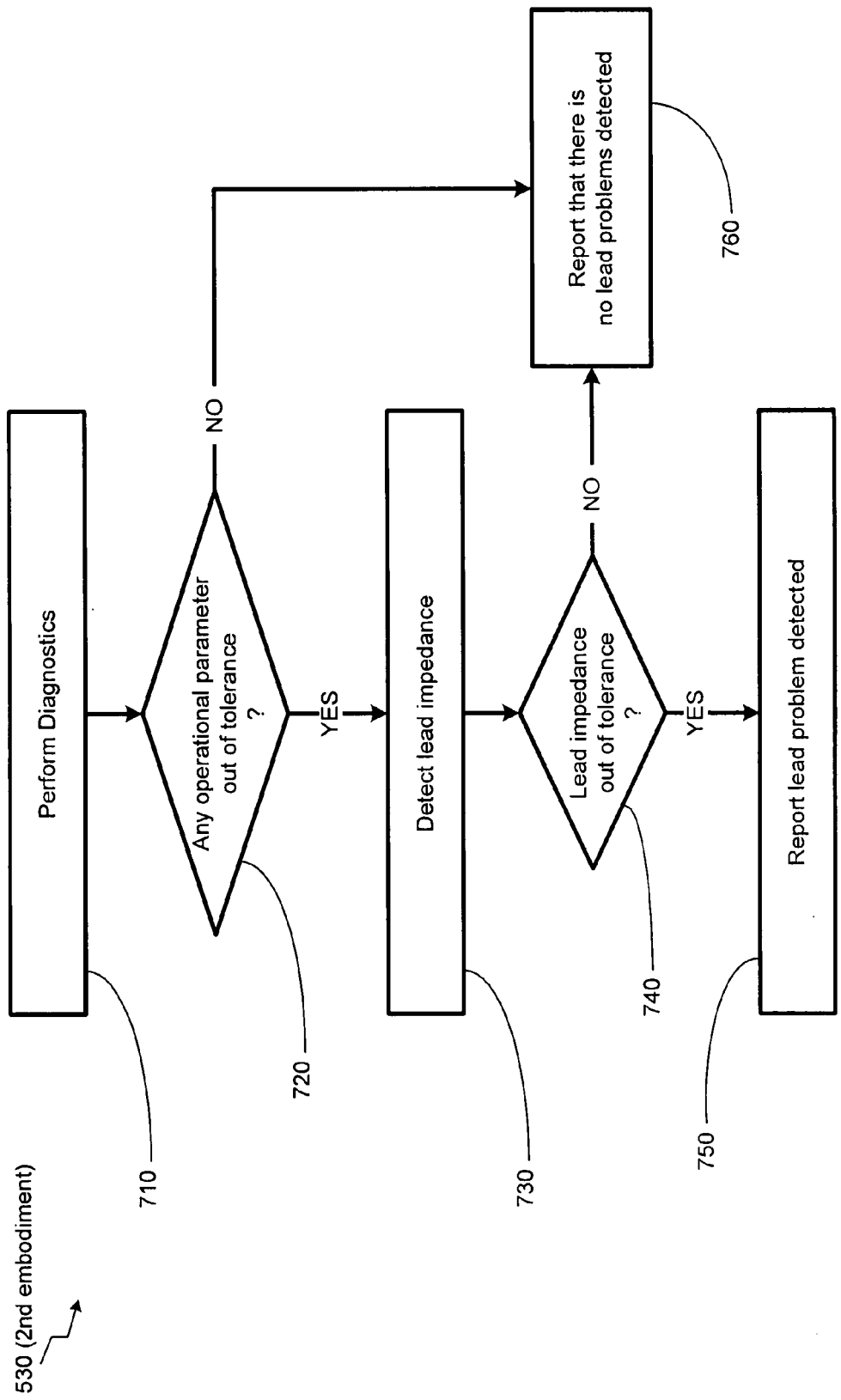
FIG. 7 illustrates a flow chart depiction of a second embodiment of performing a lead condition evaluation process of FIG. 5, in accordance with one illustrative embodiment of the present invention.

Turning now to FIG. 7, another flowchart depiction of performing the lead health evaluation process of block 530 of FIG. 5, in accordance with a second embodiment of the present invention, is provided. In order to perform a lead condition evaluation process, in this embodiment, the IMD 200 may perform a diagnostics analysis (block 710) of the IMD 200. Impedance measurements are used to assess the integrity of the electrical leads that deliver the stimulation provided by a pulse generator. The diagnostics performed by the IMD 200 may be performed as a result of a routine predetermined regimen and/or a signal to perform the diagnostics based upon operation of the IMD 200, such as a flag set by a block described in connection with FIG. 2, based upon sensing of any operational parameter associated with the operation of the IMD 200. The IMD 200 may then determine whether any operational parameter is out of tolerance or is not within an acceptable range of accepted values (block 720). The operational parameters may include, but are not limited to, battery consumption, high current values, low current values, power output, energy output, which may be power output per unit of time, charge delivered per pulse, and/or other diagnostics results.

Based upon a detection that an operational parameter is out of tolerance, the IMD 200 may be prompted to perform a lead impedance detection as a result (block 730). The lead impedance may be measured in various manners, such as the process described above. Once the lead impedances are determined, a determination is made whether the lead impedance is out of tolerance or not within acceptable range of values (block 740). Upon a determination that the lead impedance is not out of tolerance, the IMD 200 may report that no lead problem has been detected (block 760). Upon a detection that the lead impedance is, indeed, out of tolerance, a report may be provided by the IMD 200 that there is, indeed, a possible lead condition problem (block 750). The IMD 200 may then utilize the results of description provided in FIG. 6 to perform corrective action.

Those skilled in the art would appreciate that methods illustrated in FIGS. 6 and 7 relate to exemplary embodiments, and that other embodiments may be implemented by those skilled in the art having benefit of the present disclosure and remain within the spirit and scope of the present invention. Alternative embodiments may include using other tests and algorithms (e.g., such as combining various portions of FIGS. 6 and 7).

Figure 8:
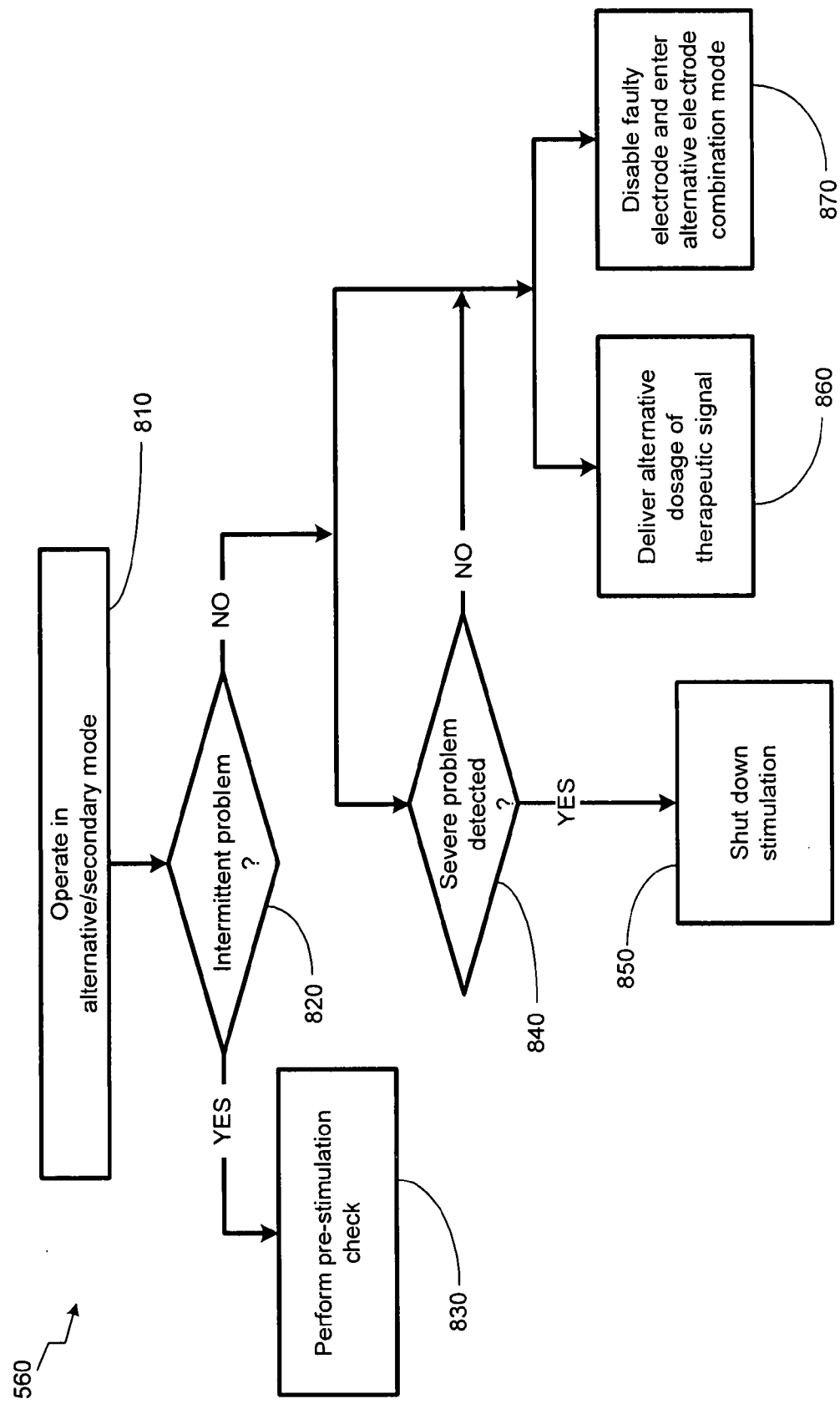
FIG. 8 illustrates a flow chart depiction of a step for entering an alternative/secondary operation mode of the IMD, in accordance with one illustrative embodiment of the present invention.

Turning now to FIG. 8, a flowchart depiction of the step of entering an alternative/secondary operation mode of block 560 of FIG. 5 in response to a determination that a lead problem exists (block 540), is provided in accordance with one illustrative embodiment of the present invention. Upon detecting a lead problem, as described in block 540, the IMD 200 may change its operation and enter into an alternative/secondary mode (block 810). The alternative/secondary operation mode may include a variety of operating features understandable by those skilled in the art having benefit of the present disclosure. For example, the IMD 200 may determine whether the detected lead condition problem is an intermittent problem (block 820). As described above, various statistical analyses of data associated with examining the lead condition/health may be indicative of whether a lead condition is intermittent or not.

Upon a determination that a lead problem is, indeed, an intermittent problem, a pre-stimulation check may be performed by the IMD 200 (block 830). The pre-stimulation check may include a variety of types of diagnostics that may be performed prior (e.g., substantially immediately prior) to delivery of a therapeutic electrical signal burst (i.e., a serious of pulses comprising a therapeutic signal event). At a predetermined moment before a stimulation signal is delivered by the IMD, a pre-stimulation check may determine whether an immediate lead health issue exists or not. In some cases, the lead problem may only exist when the patient's body is in a certain position, therefore, a quick diagnostic check of the lead condition may be performed before the delivery of a therapeutic electrical signal burst. Upon an indication that the pre-stimulation check results in a determination that there is no lead problem, a burst of the therapeutic electrical signal may actually be delivered to the target tissue. If the pre-stimulation check indicates that there is a lead problem, the delivery of the stimulation signal may be delayed until a subsequent pre-stimulation check is performed and indicates the absence of a lead problem.

Upon a determination that the lead health problem is not an intermittent or occurrence, various actions may be performed, as exemplified in FIG. 8. For example, when it is determined that the lead condition problem is not intermittent, a subsequent check is made to determine whether the lead problem is a severe problem (block 840). Various predetermined definitions of a "severe" lead health problem may be pre-defined by those skilled in the art having benefit of the present disclosure. For example, an absolute lead break indicated by inordinately large lead impedance may be indicative that there is a substantial lead break. In this case, wherein a severe or significant lead problem is detected, the IMD 200 may shut down stimulation process (block 850). Severe or significant lead problems may include, but are not limited to, a substantial lead break that may cause pain and/or severely hamper the operations of the IMD 200. It will be appreciated that, although the present invention describes determining whether the problem is a severe or significant problem or not, additional determinations may be made as to whether or not the problem is major, minor or even trivial, with appropriate remedial actions taken in each case.

Referring again to FIG. 8, upon a determination that the lead problem is not intermittent, and it is determined that the lead problem is not severe, various additional steps, such as delivering alternative dosage of therapeutical signals, may be performed (block 860). The alternative dosage of therapeutical signal may include a reduction in the number of pulses delivered, an increase in the time period relating to the "off time," a reduction in the current amplitude, a reduction in the frequency of the pulse train of the therapeutic pulse signal, a decrease in pulse width, combinations of the foregoing, randomizing one or more parameters defining the therapeutic electrical signal, etc.

Alternatively, the IMD 200 may simply disable an electrode associated with a faulty lead and enter an "alternative electrode combination mode" (block 870). The alternative electrode combination mode may include changing the usage of electrode combination to avoid the electrode associated with the problematic lead. For example, a unipolar delivery of stimulation may be performed wherein the anode and cathode associated with the delivery of the stimulation signal may be defined by one electrode and the case or shell 121 associated with the IMD 200. Alternatively, other combination of electrodes may be used when avoiding a particular electrode associated with a faulty lead. In this manner, various other alternative therapeutical processes may be implemented by those skilled in the art having benefit of the present disclosure and remain within the spirit and scope of the present invention.

Figure 9:
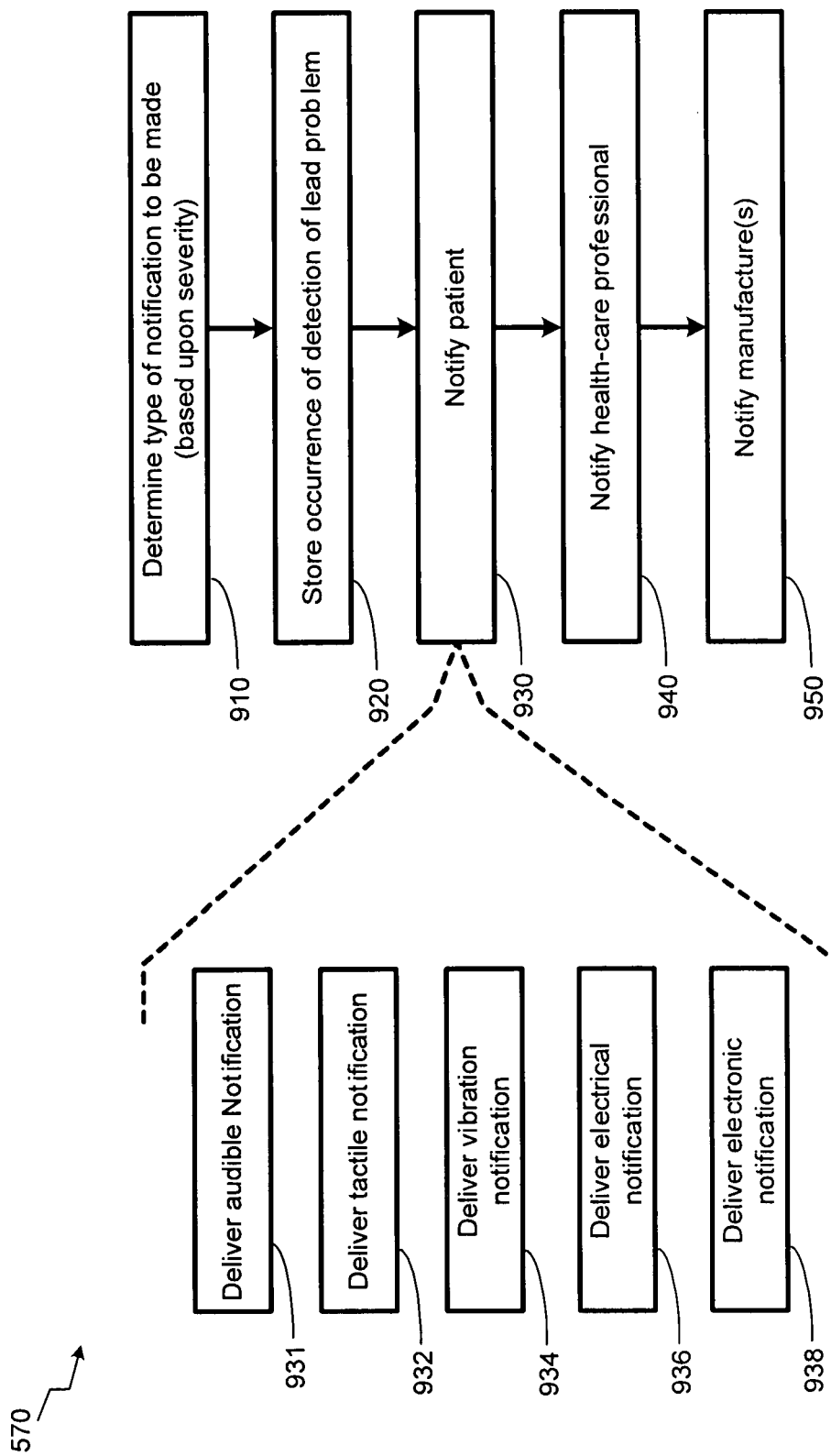
FIG. 9 illustrates a flow chart depiction of performing a notification function process of FIG. 5, in accordance with one illustrative embodiment of the present invention.

Turning now to FIG. 9, a flowchart depiction of the process associated with performing a notification function of block 570 of FIG. 5, in accordance with one illustrative embodiment of the present invention, is provided. Upon a detection that there is, indeed, a lead health problem, the IMD 200 may determine the type of notification to be made (block 910). This determination may be made based upon the severity of the problem detected. Based upon the type of notification to be made, various actions may be performed by the IMD 200. For example, the IMD 200 may store data relating to the occurrence of the detection of the lead problem (block 920), such as what measurement(s) were outside acceptable tolerances, and the time at which the unacceptable values occurred. This storage may provide for a flag that may be detected by the external unit 270 at any given time. Further, the IMD 200 may notify the patient (block 930). Notification to the patient may take on various forms, such as delivering an audible notification to the patient (block 931). Other notifications to the patient, such as delivering tactile notification (block 932), delivering vibration notification (block 934), delivering electrical notification (block 936), delivering electronic notification (block 938), and/or other types of notification to the patient may be performed. These notifications described above may be performed by the IMD 200 itself such that the patient efficiently receives these notifications. The electronic modification of block 938 may include email notices to a central database or a computer accessible by the patient, radio frequency signals, such as delivery of the signal to any a receiving device, such as a radio.

Other notifications, such as notifying a health care professional, may also be performed (block 940). Electronic communications to a database associated with a doctor's office, for example, may be performed by the IMD 200. Other indications may include prompting the patient to notify the doctor. Further, the IMD 200 may notify manufacturers associated with one or more components of the IMD system described herein (block 950). For example, the recipients may include the manufacturer of the IMD 200, the manufacturer of the leads, the manufacturer of the electrodes, etc., and may be notified automatically upon detection of the lead problem.

In this manner, automated response to the detection of lead health problems may be performed and notifications may be stored and sent. This provides for more efficient analysis and reaction to detected problems, while maintaining as much therapeutic stimulation capability as possible.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the invention. Accordingly, the protection sought herein is as set forth in the claims below.

What is claimed:

1. A method comprising:
   determining first impedance associated with a lead assembly of an implantable medical device;
   determining whether the first impedance is within an acceptable range;
   determining at least one parameter associated with the lead assembly when the first impedance is out of the acceptable range;
   analyzing the at least one parameter to determine whether a lead assembly problem is intermittent;
   performing a pre-stimulation check prior to delivery of a therapeutic electrical signal when the lead assembly problem is intermittent;
   delivering the therapeutic electrical signal when the pre-stimulation check indicates that the lead assembly is functional; and
   delaying delivery of the therapeutic electrical signal when the pre-stimulation check indicates that the lead assembly is not functional.

2. The method of claim 1, wherein determining the first impedance comprises:
   providing a controlled current signal through a first terminal and a second terminal associated with the lead assembly;
   measuring a voltage across the first and second terminals during at least a portion of a time period during which the controlled current signal is provided through the first and second terminals to determine a measured voltage; and
   determining the first impedance based upon the controlled current signal and the measured voltage.

3. The method of claim 2, wherein the controlled current signal is a test pulse that has a small magnitude compared to the therapeutic electrical signal.

4. The method of claim 2, wherein an impedance value of a first lead is subtracted from an impedance determined from the controlled current signal and the measured voltage to generate the first impedance.

5. The method of claim 1, further comprising preventing the implantable medical device from providing the therapeutic electrical signal when the lead assembly problem is determined to be a significant problem.

6. The method of claim 1, wherein the implantable medical device enters a secondary mode from a normal mode of operation when the lead assembly problem is determined to exist.

7. The method of claim 6, wherein, when the implantable medical device is in the secondary mode, the method further comprises:
   shutting down an operation of the implantable medical device;
   altering a dosage of the therapeutic electrical signal;
   disabling an electrode associated with the lead assembly; or combinations thereof.

8. The method of claim 7, wherein altering the dosage comprises reducing a number of pulses in the therapeutic electrical signal, increasing a time period of off time, reducing current amplitude of the therapeutic electrical signal, reducing a frequency of a pulse train of the therapeutic electrical signal, decreasing a pulse width of the therapeutic electrical signal, or combinations thereof.

9. The method of claim 1, further comprising performing a notification process when the lead assembly problem is determined to exist.

10. The method of claim 9, wherein the notification process comprises performing a patient notification process, a health-care professional notification process, a manufacturer notification process, or combinations thereof.

11. The method of claim 9, wherein the notification process comprises providing an audible notification, a tactile notification, a vibration notification, an electrical notification, an electronic notification, or combinations thereof.

12. A method comprising:
   determining via a controller of an implantable medical device whether an impedance associated with a lead assembly of the implantable medical device is within an accepted range;
   performing at least one test to generate data associated with the lead assembly when the impedance is not within the accepted range;
   classifying a type of problem associated with the lead assembly based on the data;
   performing a first remedial action when the type of the problem is an intermittent problem, wherein the first remedial action includes:
      performing a pre-stimulation check prior to delivery of a therapeutic electrical signal;
      delivering the therapeutic electrical signal when the pre-stimulation check indicates that the lead assembly is functional; and
      delaying delivery of the therapeutic electrical signal when the pre-stimulation check indicates that the lead assembly is not functional; and
   performing a second remedial action when the type of the problem is a second type, wherein the first remedial action is different than the second remedial action.

13. The method of claim 12, wherein classifying the type of the problem comprises determining whether the problem is the intermittent problem, a severe problem, a significant problem, or combinations thereof.

14. The method of claim 12, wherein the second remedial action comprises stopping application of therapeutic electrical signals by the implantable medical device, modifying at least one electrical parameter of the therapeutic electrical signals provided by the implantable medical device, running a pre-stimulation diagnostic check prior to delivering the therapeutic electrical signal, disabling an electrode associated with the lead assembly, or combinations thereof.

15. The method of claim 12, wherein the at least one test comprises a current output test, a lead impedance test, a power output test, an energy output test, a charge imbalance test, a compensation voltage test, or combinations thereof.

16. A method comprising:
   monitoring a lead condition of a lead assembly of an implantable medical device configured to provide therapeutic electrical signals;
   receiving data that indicates a lead condition problem;
   performing a lead condition analysis to classify a type of the lead condition problem;
   preventing the implantable medical device from providing the therapeutic electrical signals when the type of the lead condition problem is a severe problem; and
   implementing a secondary operation mode of the implantable medical device when the type of the lead condition problem is other than the severe problem by:
      performing a pre-stimulation check regimen prior to providing a therapeutic electrical signal of the therapeutic electrical signals when the type is an intermittent problem; and
      implementing one of an alternate dosage of the therapeutic electrical signals applied by the implantable medical device or a change in an electrode configuration when the type is neither the intermittent problem nor the severe problem.

17. The method of claim 16, further comprising providing a notification to a patient, a health-care professional, a manufacturer of at least a portion of the implantable medical device, a manufacturer of at least a portion of the lead assembly in response to detecting the lead condition problem, or combinations thereof.

18. The method of claim 16, wherein the lead condition analysis comprises:
   detecting a lead impedance;
   determining whether the lead impedance is outside a predetermined range;
   performing a diagnostic function in response to a determination that the lead impedance is outside the predetermined range to generate diagnostic data; and
   performing a statistical analysis of the diagnostic data.

19. The method of claim 16, wherein the implantable medical device is configured to provide cranial nerve stimulation.

20. The method of claim 16, wherein the alternate dosage comprises a reduction in a number of pulses, an increase in a period of off time, a reduction in current amplitude, a reduction in a frequency of a pulse train of the therapeutic electrical signal of the therapeutic electrical signals, a decrease in pulse width, or combinations thereof.

21. A non-transitory computer readable medium comprising instructions, that when executed by a processor, cause the processor to perform operations including:

performing at least one test to generate data associated with a lead assembly of an implantable medical device when an impedance associated with the lead assembly is outside of an accepted range;

detecting that a problem is associated with the lead assembly based on the at least one test;

classifying a type of the problem associated with the lead assembly;

implementing a first remedial action when the type of the problem is a first type by:
  performing a pre-stimulation check before initiation of a therapeutic electrical signal from the implantable medical device to a patient when the type of the problem is an intermittent problem;
  initiating the therapeutic electrical signal when the pre-stimulation check indicates that there is no lead assembly problem; and
  delaying the therapeutic electrical signal when the pre-stimulation check indicates existence of the lead assembly problem; and implementing a second remedial action when the type of the problem is a second type, wherein the first remedial action is different than the second remedial action.

22. The non-transitory computer readable medium of claim 21, wherein the at least one test comprises a current output test, a lead impedance test, a power output test, an energy output test, a charge imbalance test, a compensation voltage test, or combinations thereof.

23. The non-transitory computer readable medium of claim 21, wherein operations further include, in response to detecting the problem, providing a notification to the patient, a health-care professional, a manufacturer of at least a portion of the implantable device, a manufacturer of at least a portion of the lead assembly, or combinations thereof.

24. The non-transitory computer readable medium of claim 21, wherein the operations implementing the first remedial action include preventing application of the therapeutic electrical signal from the implantable medical device to the patient when the type of the problem is a severe problem.

* * * * *